United States Patent
Piotrowski et al.

(10) Patent No.: US 9,738,774 B2
(45) Date of Patent: Aug. 22, 2017

(54) FLAME RETARDANT FOR EPOXY RESIN CONTAINING PHOSPHONATE AND PHOSPHINATE FUNCTIONALITY

(71) Applicant: ICL-IP America Inc., Ardsley, NY (US)

(72) Inventors: Andrew M. Piotrowski, Yorktown, NY (US); Mayank P. Singh, White Plains, NY (US); Kali A. Suryadevara, Pleasantville, NY (US); Mariya Kozytska, Boston, MA (US); Yossi Zilberman, Haifa (IL)

(73) Assignee: ICL-IP America Inc., Tarrytown, NY (US)

( * ) Notice: Subject to any disclaimer, the term of this patent is extended or adjusted under 35 U.S.C. 154(b) by 71 days.

(21) Appl. No.: 15/040,100

(22) Filed: Feb. 10, 2016

(65) Prior Publication Data
US 2016/0244596 A1   Aug. 25, 2016

Related U.S. Application Data

(60) Provisional application No. 62/118,011, filed on Feb. 19, 2015.

(51) Int. Cl.
*B32B 9/04* (2006.01)
*C08K 5/5313* (2006.01)
(Continued)

(52) U.S. Cl.
CPC .............. *C08K 5/5313* (2013.01); *B32B 5/26* (2013.01); *B32B 7/12* (2013.01); *B32B 15/08* (2013.01); *B32B 15/20* (2013.01); *B32B 27/06* (2013.01); *B32B 37/10* (2013.01); *C07F 9/657172* (2013.01); *C07F 9/657181* (2013.01); *C08G 59/4071* (2013.01); *C08G 59/621* (2013.01); *C08G 59/686* (2013.01); *C08J 5/24* (2013.01); *C08L 63/04* (2013.01); *H05K 1/0373* (2013.01); *B32B 37/06* (2013.01); *B32B 2255/26* (2013.01); *B32B 2260/021* (2013.01); *B32B 2260/046* (2013.01); *B32B 2262/101* (2013.01);
(Continued)

(58) Field of Classification Search
CPC ............ H05K 1/0373; H05K 2201/012; C07F 9/657172; C07F 9/657181; C08G 59/4071
See application file for complete search history.

(56) References Cited

U.S. PATENT DOCUMENTS 7,148,312 B2   12/2006   Kim et al.
8,580,984 B2   11/2013   Kersbulck et al.
(Continued)

FOREIGN PATENT DOCUMENTS

CN   104109347 A   10/2014
CN   104736598 A   6/2015
(Continued)

OTHER PUBLICATIONS

U.S. Appl. No. 62/254,847 dated Nov. 13, 2015.

*Primary Examiner* — Eisa Elhilo
(74) *Attorney, Agent, or Firm* — Dilworth & Barrese, LLP

(57) ABSTRACT

There is provided herein a curing agent compound for curing thermosetting resins, e.g., epoxy resins, a composition comprising a thermoplastic and/or thermosetting resin, e.g., an epoxy resin and the curing agent, an article comprising the curing agent, and a method of making the curing agent.

19 Claims, 4 Drawing Sheets

(51) Int. Cl.

| | | |
|---|---|---|
| *C07F 9/6571* | (2006.01) | |
| *C08J 5/24* | (2006.01) | |
| *C08G 59/40* | (2006.01) | |
| *B32B 15/20* | (2006.01) | |
| *H05K 1/03* | (2006.01) | |
| *B32B 37/10* | (2006.01) | |
| *C08G 59/62* | (2006.01) | |
| *C08G 59/68* | (2006.01) | |
| *C08L 63/04* | (2006.01) | |
| *B32B 5/26* | (2006.01) | |
| *B32B 7/12* | (2006.01) | |
| *B32B 15/08* | (2006.01) | |
| *B32B 27/06* | (2006.01) | |
| *B32B 37/06* | (2006.01) | |

(52) U.S. Cl.
CPC . *B32B 2307/3065* (2013.01); *B32B 2309/125* (2013.01); *B32B 2311/12* (2013.01); *B32B 2457/08* (2013.01); *C08J 2363/04* (2013.01); *H05K 2201/012* (2013.01)

(56) References Cited

U.S. PATENT DOCUMENTS

| | | |
|---|---|---|
| 8,669,333 B2 | 3/2014 | Arita et al. |
| 2012/0055705 A1* | 3/2012 | White ............... C07F 9/657172 174/259 |
| 2015/0118499 A1 | 4/2015 | Suzuki et al. |

FOREIGN PATENT DOCUMENTS

| | | |
|---|---|---|
| JP | 2013057853 A1 | 3/2013 |
| KR | 2014168794 A | 11/2014 |

* cited by examiner

FLAME RETARDANT FOR EPOXY RESIN CONTAINING PHOSPHONATE AND PHOSPHINATE FUNCTIONALITY

FIELD OF THE INVENTION

The present invention relates to the field of flame retardants, specifically phosphorous-containing flame retardants for electronic applications such as printed wiring boards.

BACKGROUND OF THE INVENTION

Synthetic resins are widely used in both industrial and consumer electronics because of among other things, their chemical resistance, mechanical strength and electrical properties. For example, synthetic resins can be used in electronics as protective films, adhesive materials and/or insulating materials, such as interlayer insulating films. To be useful for these applications, the synthetic resins need to provide ease of handling and certain necessary physical, thermal, electrical insulation and moisture resistance properties. For example, synthetic resins having a low dielectric constant, and a low moisture uptake as well as a high glass transition temperature (Tg) can be a desirable combination of properties for electronic applications.

Synthetic resins, however, can be flammable. As such, different approaches have been made to impart a desired level of flame resistance to synthetic resins, e.g., epoxy resin, where such approaches entail employing either halogen-free flame retardant compounds or halogen-containing flame retardant compounds. Halogenated compounds, however, are now undergoing additional scrutiny, and the various non-halogenated compounds available do not provide the desired level of flame retardancy to the synthetic resin. It would be desirable to provide a desired level of flame retardancy to a synthetic resin such as an epoxy resin while still maintaining a suitable combinations of properties for electronic applications.

SUMMARY OF THE INVENTION

It is therefore a feature of the present invention to provide a compound(s), which can function as a halogen-free curing agent for thermosetting resins, e.g., epoxy resins, which cured epoxy resins can be employed in electronic applications while maintaining a low dielectric constant, and a low moisture uptake as well as a high glass transition temperature (Tg).

It will be understood herein that in one non-limiting embodiment the expression "halogen-free curing agent for epoxy resins" can be used interchangeably with "halogen-free curing agent for epoxy resins", "epoxy curing agent", "curing agent for epoxy", "epoxy resin curing agent" and "curing agent", and the like.

There is provided herein in one embodiment herein a compound having the general formula (I):

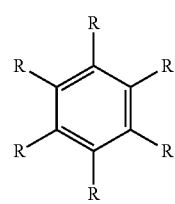

(I)

wherein each R is independently selected from H; —OH; an alkyl containing from 1 to about 8 carbon atoms;

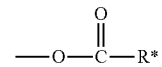

where R* is an alkyl group containing from 1 to 8 carbon atoms or a substituted or unsubstituted phenyl;

a phosphinate moiety of the formula (II):

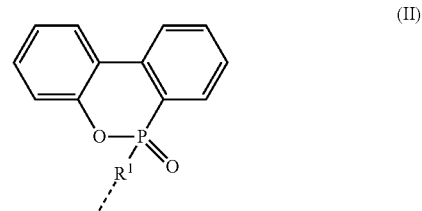

(II)

wherein $R^1$ is a divalent linear or branched alkylene moiety of from 1 to 3 carbon atoms, and the dashed line represents a bond to the structure of formula (I) above;

a phosphonate moiety of the general formula (III):

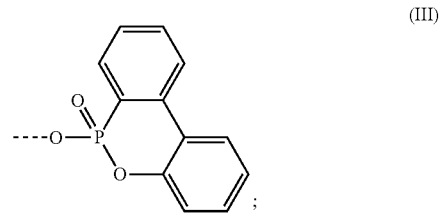

(III)

and, a substituted aryl moiety of the general formula (IV):

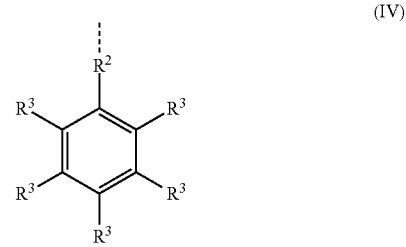

(IV)

where $R^2$ is a divalent linear or branched alkylene moiety of from 1 to 4 carbon atoms, and the dashed line represents a bond to the structure of formula (I) above, and $R^3$ is defined the same as R except that $R^3$ cannot be the substituted aryl moiety of the general formula (IV) and at least one $R^3$ is a group of the formula (II);

and provided that the number of R groups of the formula (I) which are of the formula (II) are 1 or 2, the number of R groups of the formula (I) which are of the formula (III) are 1 or 2 and provided that none of the R groups or only one of the R groups of formula (I) are of the formula (IV), and further provided that when none of the R groups of the formula (I) are of the formula (IV), then the total number of R groups which are of the formula (II) and (III) can be up to 4, and if one of the R groups of the formula (I) is of the formula (IV) then the total number of R groups which are of the formula (II), (III) and (IV) are up to four.

It will be understood herein that the compound of the formula (I) as described herein can function as a curing agent for curing thermosetting resins, e.g., epoxy resin, as described herein or in another embodiment as a (Reactive flame retardant) flame retardant additive for thermoplastic resin compositions and/or formulations.

DETAILED DESCRIPTION OF THE INVENTION

Figure 1:
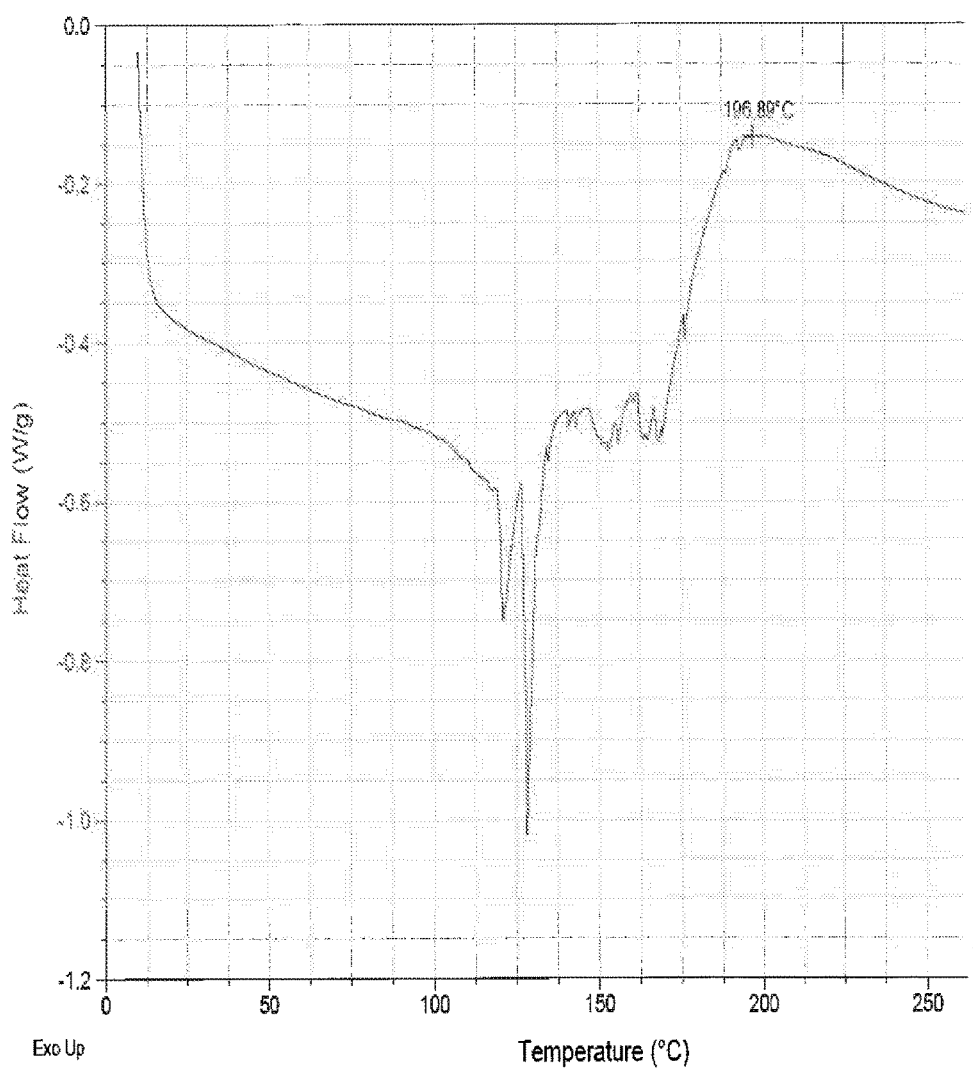
FIG. 1 is a DSC graph produced at 10° C./min using Compound 1 of Synthesis Example 1 as used in a laminate as is described in laminate Example 2.

The present invention is directed to compound(s), which can function as a halogen-free curing agent(s) for thermosetting resins, e.g., epoxy resins, which cured epoxy resins can be employed in any commercial or industrial epoxy application which requires a flame retardant such as the non-limiting example of electronic applications while maintaining a low dielectric constant, and a low moisture uptake as well as a high glass transition temperature (Tg). Advantageously herein, the compound(s) which function as a halogen-free curing agent for thermosetting resins, e.g., epoxy resins, when reacted with epoxy resins, the products are in the absence of hydroxyl groups, such as secondary hydroxyl groups thus, avoiding the high water absorption and higher dielectric constant of conventional curing systems, which when reacted with epoxy the products therein contain such secondary hydroxyl groups. In addition, the halogen-free curing agent(s) described herein can be used as a flame retardant additive in thermoplastic compositions and/or formulations while maintaining optimal properties of the thermoplastic material.

Some more specific embodiments of compound(s) which can be used as the curing agent compound for curing thermosetting resins, e.g., epoxy resin, is wherein the compound is selected from any one or more of the formulae (V)-(XI):

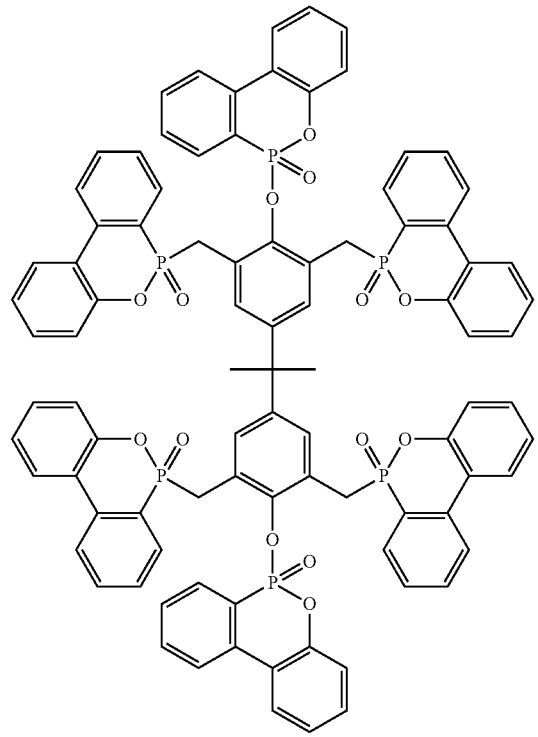

(V)

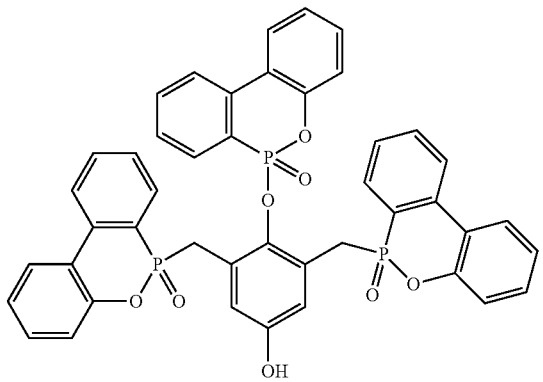

(VI)

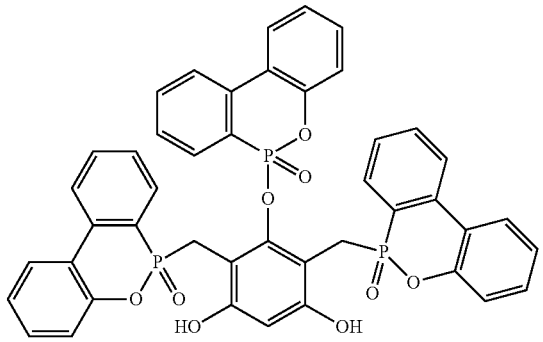

(VII)

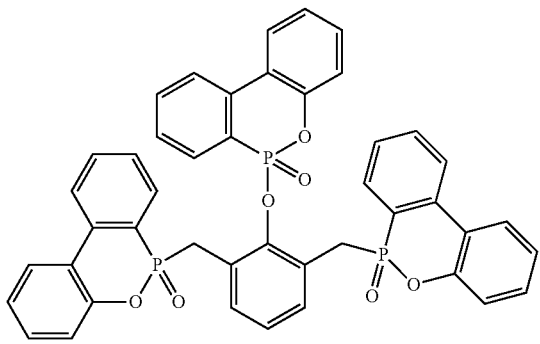

VIII

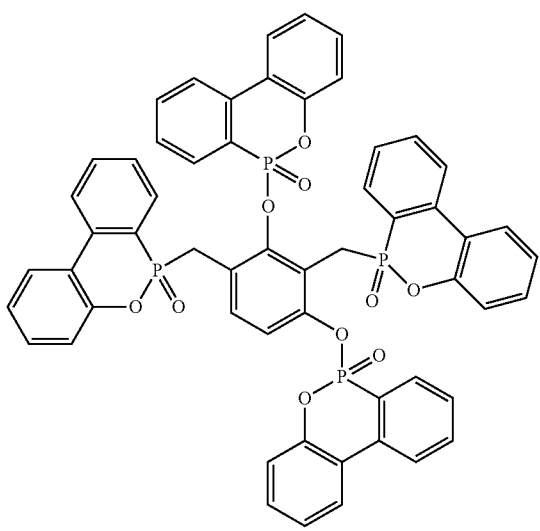

IX

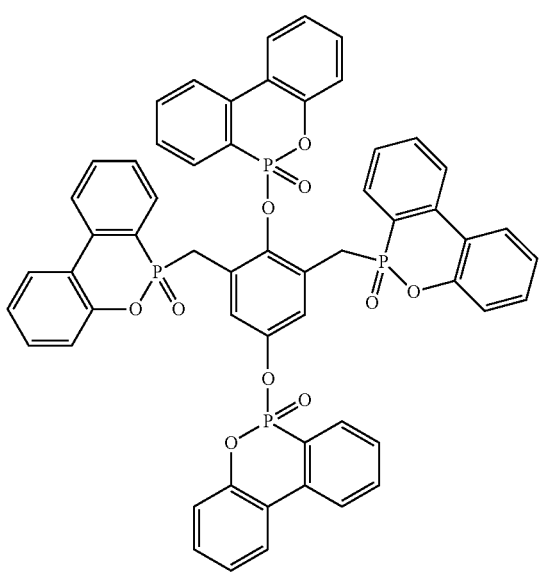

(X)

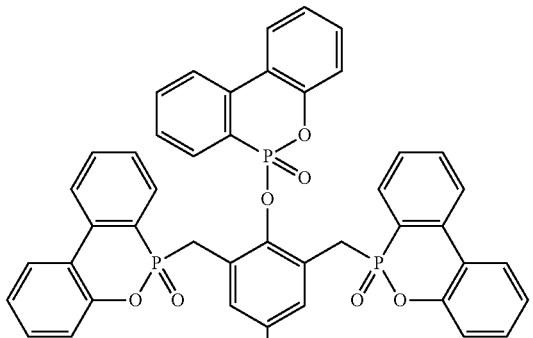

(XI)

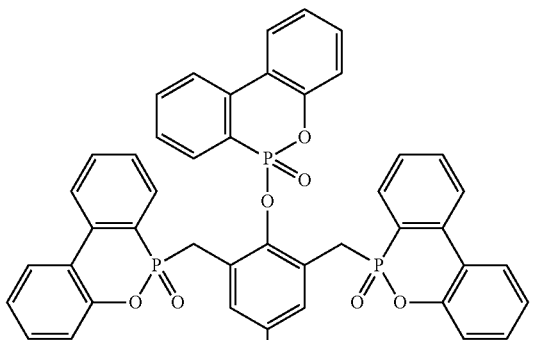

(XII)

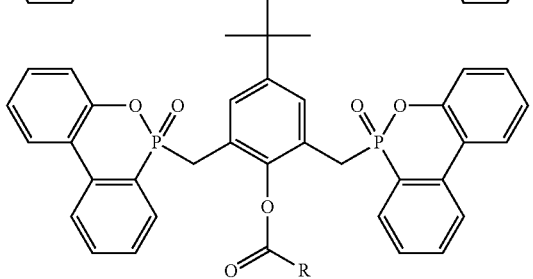

In one embodiment, the compound(s) which can be used as the curing agent compound for curing thermosetting resins, e.g., epoxy resin (e.g., the halogen-free curing agent for epoxy resins described herein) can be a phosphorus containing compound such as those having at least one phosphonate group and at least one phosphinate group per molecule, and a phosphorus content of at least 4 wt-percent. And more preferably, the phosphorus containing compounds are those having at least one phosphonate group and at least one phosphinate group per molecule and phosphorus content of 6%. The compounds (I) and/or (V)-(XI) described herein meet these requirements and are preferably substantially free (or completely free) of bromine atoms, and more preferably substantially free (or completely free) of halogen atoms. Compounds (I) and/or (V)-(XI) described herein may also be used as a non-reactive additive, such as when used with a thermoplastic or other thermosetting systems, e.g., other than epoxy. For example, Compound (I) and/or (V)-(XI) noted above can be used a charring agent to provide an insulating layer of char at elevated temperatures for thermoplastic formulations and for thermosetting formulations and they can also act in the vapor phase)

The terms halogen-free curing agent refers to an aromatic (ester that can react with epoxy according to the following scheme:

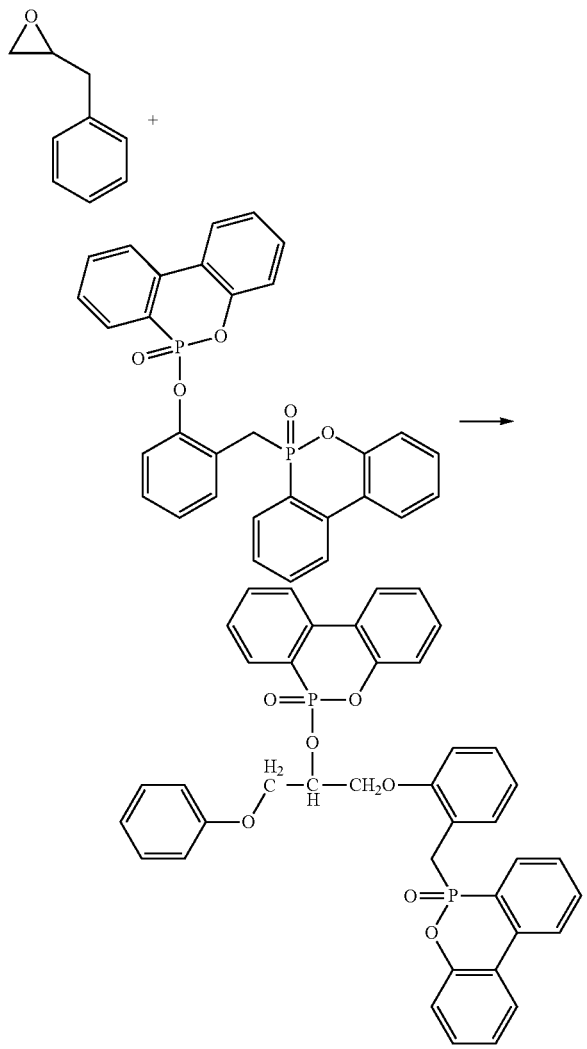

wherein R as defined here for the above scheme can be a linear or branched alkyl of from 1 to 6 carbon atoms or a non-substituted phenyl or a substituted phenyl containing up to about 12 carbon atoms, wherein the substituted phenyl can be substituted with a linear or branched alkyl of from 1 to 6 carbon atoms.

In contrast to a conventional epoxy curing scheme:

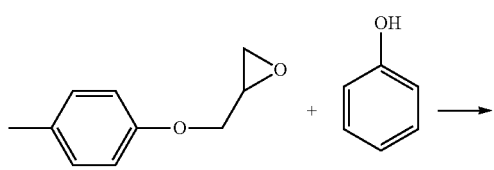

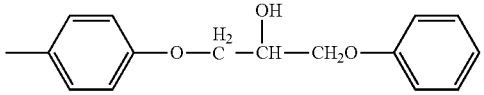

In one embodiment herein there are provided compounds, compositions and/or formulations obtainable by reacting, blending or mixing Compound (I), and/or the related compounds (V)-(XI) with other components such as a thermosetting resin or a thermoplastic material or a mixture of a thermosetting resin and a thermoplastic material to form various ignition resistant compounds, compositions or formulations useful in various applications such as prepregs, laminates, coatings, molding articles and composite products.

Another embodiment herein is directed to phosphorous-containing epoxy resin curable formulations comprising (i) Compound (I), and/or the related compounds (V)-(XI) (ii) an epoxy resin or a mixture of epoxy resins, (iii) optionally, a co-crosslinker, (iv) optionally, a curing catalyst, and (v) optionally, a Lewis acid.

Yet in another embodiment herein there is provided a curable flame-resistant epoxy resin composition comprising (i) the above phosphorus-containing compound (e.g., Compound (I), and/or (V)-(XI)), (ii) optionally, a benzoxazine-containing compound, (iii) a crosslinkable epoxy resin or a blend of two or more epoxy resins having more than one epoxy group per molecule, (iv) optionally a co-crosslinker and, (v) optionally, a curing catalyst to obtain a curable flame resistant epoxy resin composition. Such curable flame resistant epoxy resin compositions may be used to make prepregs, which prepregs may be used to make laminates and circuit boards useful in the electronics industry. The epoxy resin composition may also be used to coat metallic foils such as copper foils to make resin coated copper foils for so called build-up technology.

The phosphorus-containing compounds, (Compounds (I), and/or (V)-(XI)) described herein), and derivatives thereof, may also be combined with at least one thermoplastic resin to make an ignition-resistant thermoplastic composition.

The phosphorus-containing compounds, (Compounds (I), and/or (V)-(XI) described herein) and derivatives thereof, may also be combined with at least one thermoplastic resin and thermosetting systems (epoxy and curing agents) to make a hybrid ignition-resistant thermoplastic containing thermosetting composition.

Ignition Resistant Epoxy Resin Composition (Epoxy Resin Composition)

In one embodiment of the present invention, the phosphorus-containing compound (I), and/or (V)-(XI) described herein as well in one embodiment, combinations thereof, may be used, as one component, of a curable (crosslinkable) phosphorus-containing flame resistant epoxy resin composition. In this embodiment, the curable phosphorus-containing flame-resistant epoxy resin composition comprises (i) the phosphorus-containing compound, Compound (I), and/or (V)-(XI) described herein, (ii) at least one epoxy resin such as those selected from halogen-free epoxies, phosphorus-free epoxies, and phosphorus-containing epoxies and mixtures thereof, including, but not limited to DEN 438, DER 330, EPON 164 (DEN and DER are trademarks of The Dow Chemical Company), epoxy functional polyoxazolidone containing compounds, cycloaliphatic epoxies, GMA/styrene copolymers, and the reaction product of DEN 438 and DOPO resins; and optionally (iii) at least one co-crosslinker, and optionally one or more of a curing catalyst, a Lewis acid, an inhibitor, and a benzoxazine-containing compound. The curable phosphorous containing flame resistant epoxy resin composition optionally may contain at least one additional crosslinkable epoxy resin or a blend of two or more epoxy resins other than and different from component (ii) above. The curable phosphorous-containing flame resistant epoxy resin composition may also optionally contain at least one curing catalyst and at least one inhibitor. All of the above components may be blended or mixed together in any order to form the curable phosphorus-containing flame-resistant epoxy resin composition.

The curable phosphorous-containing flame resistant epoxy resin compositions prepared according to the present invention, whether made either by reacting a mixture of Compound (I), and/or Compounds (V)-(XI) described herein, an epoxy resin, and optionally another co-crosslinker (i.e. another curing agent); may be used to make prepregs, which, in turn, may be used to make laminates and circuit boards useful in the electronics industry. The phosphorous-containing flame resistant epoxy resin compositions may also be used to coat metallic foils such as copper foils to make resin coated copper foils for so called build-up technology.

The epoxy resins which can be used in the herein described invention include, in one embodiment, polyepoxides having the following general Formula (XII):

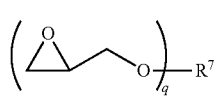

(XII)

wherein "$R^7$" is substituted or unsubstituted aromatic, aliphatic, cycloaliphatic or heterocyclic group having a valence of "q", where "q" preferably has an average value of from 1 to less than about 8. Examples of the polyepoxide compounds useful in the present invention include the diglycidyl ethers of the following compounds: resorcinol, catechol, hydroquinone, bisphenol, bisphenol A, bisphenol AP (1,1-bis(4-hydroxylphenyl)-1-phenyl ethane), bisphenol F, bisphenol K, phenol-formaldehyde novolac resins, alkyl substituted phenol-formaldehyde resins, phenol-hydroxybenzaldehyde resins, cresol-hydroxybenzaldehyde resins, dicyclopentadiene-phenol resins, dicyclopentadiene-substituted phenol resins tetramethylbiphenol, and any combinations thereof.

Examples of particular polyepoxide compounds useful in the present invention include a diglycidyl ether of bisphenol A having an epoxy equivalent weight (EEW) between 177 and 189 sold by The Dow Chemical Company under the trademark D.E.R. 330; the halogen-free epoxy-terminated polyoxazolidone resins, phosphorus element containing compounds; cycloaliphatic epoxies; and copolymers of glycidyl methacrylate ethers and styrene.

Preferred polyepoxide compounds include epoxy novolacs, such as D.E.N. 438 or D.E.N. 439 (trademarks of The Dow Chemical Company); cresole epoxy novolacs such as QUATREX 3310, 3410 and 3710 available from Ciba Geigy; trisepoxy compounds, such as TACTIX 742 (trademark of Ciba Geigy Corporation of Basel, Switzerland); epoxidized bisphenol A novolacs, dicyclopentadiene phenol epoxy novolacs; glycidyl ethers of tetraphenolethane; diglycidyl ethers of bisphenol-A; diglycidyl ethers of bisphenol-F; and diglycidyl ethers of hydroquinone.

In one embodiment, the most preferred epoxy compounds are epoxy novolac resins (sometimes referred to as epoxidized novolac resins, a term which is intended to embrace both epoxy phenol novolac resins and epoxy cresol novolac resins). Epoxy novolac resins (including epoxy cresol novolac resins) are readily commercially available, for example under the trade names D.E.N. (trademark of The Dow Chemical Company), and QUATREX and TACTIX 742 (trademarks of Ciba Geigy).

Preferred compounds of the type mentioned above have epoxy equivalent between 150-400 and most preferably from 160-300 and molecular weight above 500 and most preferable between 700-2500.

The polyepoxide useful in the present invention is preferably substantially free (or completely free) of bromine atoms, and more preferably substantially free (or completely free) of halogen atoms.

One non-limiting example of polyepoxides that are useful in the present invention and that are substantially free of halogen atoms are the phosphorus-containing epoxy resins such as those which are the reaction products of an epoxy compound containing at least two epoxy groups and a reactive phosphorus-containing compound such as 3,4,5,6-dibenzo-1,2-oxaphosphane-2-oxide (DOP), or 10-(2',5'-dihydroxyphenyl)-9,10-dihydro-9-oxa-10-phosphaphenanthrene-10-oxide (DOP-HQ).

The amount of epoxy in the compositions described herein, e.g., the curable phosphorous-containing flame resistant epoxy resin compositions, the thermoset composition and the hybrid composition is such that the final formulation of epoxy, any optional phosphorous containing epoxy, compound of the general formula (I) and/or (V)-(XI) in the amounts described herein, and any other components in the amounts described herein or known to those skilled in the art, is such that the total phosphorous content of the composition is from 1 weight percent to about 5 weight percent, more specifically from about 2 to about 3.5 weight percent. Thus, one skilled in the art will formulate the amount of epoxy to be commensurate with such other components so as to have a final phosphorous content as described above.

The amount of such phosphorus containing epoxy in the final composition can vary from 10-90 parts, preferably 20-80 parts and most preferably from 30-50 parts based on 100 parts of epoxy resin.

The amounts of epoxy resin described herein can in one non-limiting embodiment be the amounts of the thermoplastic resin in the thermoplastic composition described herein, the thermoset resin in the thermoset composition described herein and the combined amount of resins in the hybrid composition described herein.

The flame retardant effective amount of the compound (I) and/or (V)-(XI) which can be used as the compound for curing epoxy resin herein in the curable epoxy resin composition described herein will vary depending on the specific epoxy resin and the specific compound being employed as well as specific parameters of processing as are known by those skilled in the art. In one non-limiting embodiment, flame retardant effective amount of the compound (I) and/or compound (V)-(XI) which can be used for curing epoxy resin is from about 10 to about 150 parts by weight per 100 parts of the epoxy resin, more specifically from about 30 to about 100 parts by weight per 100 parts of the epoxy resin and most specifically from about 50 to about 70 parts by weight per 100 parts of the epoxy resin. To provide adequate flame retardancy the compositions herein will have from 1.0% P to about 5% P in the final composition. In one embodiment, the above stated amounts of compound (I)

and/or (V)-(XI) can be the amounts of compound (I) and/or (V)-(XI) used in any of the epoxy resin composition, the thermoplastic composition, the thermoset composition and the hybrid composition described herein.

As described above, a phosphorous-containing flame resistant epoxy resin compositions may be formed by blending (i) the phosphorus-containing product, Compound (I) and/or Compounds (V)-(XI) described herein, (ii) at least one crosslinkable epoxy compound, and optionally (iii) at least one co-crosslinker, as well as any of the other optional components described herein; or in another embodiment, the phosphorous-containing flame resistant epoxy resin compositions may be formed by blending (i) an epoxidized Compound (I) and/or Compounds (V)-(XI), at least one crosslinkable phosphorous-containing epoxy compound, and (iii) at least one co-crosslinker, as well as any of the other optional components described herein. The phosphorous-containing flame resistant epoxy resin compositions may, optionally, contain at least one crosslinkable epoxy resin other than the crosslinkable phosphorus-containing epoxy compounds in (ii) above. In one embodiment herein it will be understood that the term "crosslinkable" in crosslinkable phosphorus-containing epoxy compound is understood to be a phosphorous-containing epoxy compound which has more than 2 epoxy functionalities, as would be understood by those skilled in the art.

With any of the compositions above where an epoxy resin is present, any number of co-crosslinking agents (i.e., in addition to the phosphorous compound (I) and/or (V)-(XI)) may optionally also be used. Suitable co-crosslinkers that may optionally be present in combination with the phosphorus-containing epoxy compounds according to the present invention include, for example, are the multifunctional co-crosslinkers as are known to those in the art.

The-co-crosslinkers include, for example, copolymers of styrene and maleic anhydride having a molecular weight ($M_w$) in the range of from 1,500 to 50,000 and an anhydride content of more than 15 percent. Commercial examples of these materials include SMA 1000, SMA 2000, and SMA 3000 and SMA 4000 having styrene-maleic anhydride ratios of 1:1, 2:1, 3:1 and 4:1, respectively, and having molecular weights ranging from 6,000 to 15,000, which are available from Elf Atochem S.A.

Other preferred co-crosslinkers useful in the present invention include hydroxyl-containing compounds such as those represented by the following Formula (XIII):

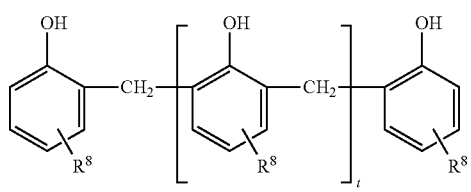

(XIII)

wherein "$R^8$" is hydrogen or an alkyl group having from 1 to 20, preferably from 1 to 10, and more preferably 1 to 5 carbon atoms and "t" is an integer of from 0 to 20, preferably from 1 to 10, and more preferably from 2 to 5.

Commercially available products having the above Formula (XIII) include, for example, PERSTORP 85.36.28, which is a phenolic resin obtained from phenol and formaldehyde having an average Mettler softening point of 103° C., melt viscosity at 150° C.=1.2 Pas and a functionality of 6 to 7. Another example includes SD1708 (from Momentive): Viscosity at 150° C., 2200-3800 cps Softening Pt: 110° C.; HRJ13399 (from SI Group): Specific Gravity 1.20, Softening Pt: 90-105; HRJ12952 (from SI Group): Specific Gravity 1.25, Softening Pt: 97-107; FRJ425 (from SI Group): Specific Gravity 1.24, Softening Pt: 112-118; BRJ 473 liquid (from SI Group): Specific Gravity 1.10, Brookfield viscosity: 1000-4500 cps.

One example of co-crosslinker that is suitable in the compositions described herein are phenolic resins with general formula (XIV):

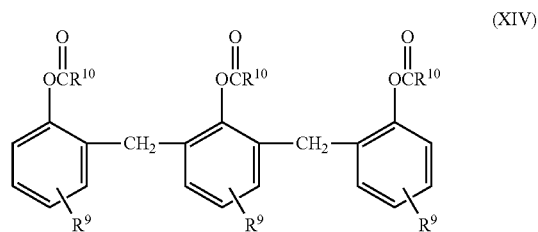

(XIV)

where $R^9$ is hydrogen, a aliphatic moiety of from 1 to 10 carbon atoms, or phenyl or a substituted phenyl; $R^{10}$ is an aliphatic moiety of from 1 to 4 carbon atoms, or a phenyl or a substituted phenyl group. One examples of a commercial curing system of this type is EPICLON HPC-S000-65T available from DIC corporation, Japan.

Other phenolic functional materials which are suitable as co-crosslinker include compounds which form a phenolic crosslinking agent having a functionality of at least 2 upon heating. Some examples of these compounds are benzoxazine groups-containing compounds. Examples of compounds which form a phenolic crosslinking agent upon heating include phenolic species obtained from heating benzoxazine, for example as illustrated in the following chemical equation:

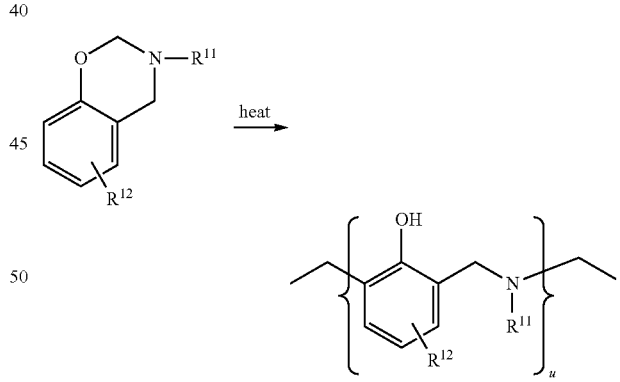

wherein "u" is greater than 1 and preferably up to about 100,000; and wherein "$R^{11}$" and "$R^{12}$" may be, independently and separately, the same or different of a hydrogen, an allyl group from 1 to about 10 carbon atoms, such as methyl, a 6 to 20 carbon atom aromatic group such as phenyl or a 4 to 20 carbon atom cycloaliphatic group such as cyclohexane.

Examples of the above compounds also include benzoxazine of phenolphthalein, benzoxazine of bisphenol-A, benzoxazine of bisphenol-F, benzoxazine of phenol novolac, and mixtures thereof. A mixture of these compounds and Formula (XI) may also be used in the present invention. Non-limiting examples of commercial benzoxazines from Huntsman include examples such as Bisphenol A benzoxazine (MT35600); Bisphenol F benzoxazine (MT35700) Phenolphthalein benzoxazine (MT35800); Thiodiphenol benzoxazine (MT35900) and, Dicyclopentadiene benzoxazine (MT36000)

When a co-crosslinker is used in the present invention, the co-crosslinker is present in an amount to crosslink of less than 50 percent of the stoichiometric amount needed to cure the thermosetting resin, e.g., the epoxy resin, is more preferably less than about 40% amount needed to cure the thermosetting resin, e.g., epoxy resin and most preferably less than about 35% amount needed to cure the thermosetting resin, e.g., epoxy resin.

Any of the curable compositions of the present invention described herein may comprise a curing catalyst. Examples of suitable curing catalyst (catalyst) materials useful in the present invention include compounds containing amine, phosphine, ammonium, phosphonium, arsonium or sulfonium moieties or mixtures thereof. Particularly preferred catalysts are heterocyclic nitrogen-containing compounds.

The catalysts (as distinguished from co-crosslinkers) preferably contain on average no more than about 1 active hydrogen moiety per molecule. Active hydrogen moieties include hydrogen atoms bonded to an amine group, a phenolic hydroxyl group, or a carboxylic acid group. For instance, the amine and phosphine moieties in catalysts are preferably tertiary amine or phosphine moieties; and the ammonium and phosphonium moieties are preferably quaternary ammonium and phosphonium moieties.

Among preferred tertiary amines that may be used as catalysts are those mono- or polyamines having an open-chain or cyclic structure which have all of the amine hydrogen replaced by suitable substituents, such as hydrocarbyl radicals, and preferably aliphatic, cycloaliphatic or aromatic radicals.

Examples of these amines include, among others, 1,8-diazabicyclo(5.4.0)undec-7-en (DBU), methyl diethanol amine, triethylamine, tributylamine, dimethyl benzylamine, triphenylamine, tricyclohexyl amine, pyridine and quinoline. Preferred amines are the trialkyl, tricycloalkyl and triaryl amines, such as triethylamine, triphenylamine, tri-(2,3-dimethylcyclohexyl)amine, and the alkyl dialkanol amines, such as methyl diethanol amines and the trialkanolamines such as triethanolamine Weak tertiary amines, for example, amines that in aqueous solutions give a pH less than 10 in aqueous solutions of 1 M concentration, are particularly preferred. Especially preferred tertiary amine catalysts are benzyldimethylamine and tris-(dimethylaminomethyl)phenol.

Examples of suitable heterocyclic nitrogen-containing catalysts include heterocyclic secondary and tertiary amines or nitrogen-containing catalysts which can be employed herein include, for example, imidazoles, benzimidazoles, imidazolidines, imidazolines, oxazoles, pyrroles, thiazoles, pyridines, pyrazines, morpholines, pyridazines, pyrimidines, pyrrolidines, pyrazoles, quinoxalines, quinazolines, phthalozines, quinolines, purines, indazoles, indoles, indolazines, phenazines, phenarsazines, phenothiazines, pyrrolines, indolines, piperidines, piperazines and combinations thereof. Especially preferred are the alkyl-substituted imidazoles; 2,5-chloro-4-ethyl imidazole; and phenyl-substituted imidazoles, and mixtures thereof. Even more preferred are N-methylimidazole; 2-methylimidazole; 2-ethyl-4-methylimidazole; 1,2-dimethylimidazole, and 2-methylimidazole and mixtures thereof. Especially preferred is 2-phenylimidazole.

The amount of curing catalyst used depends on the molecular weight of the catalyst, the activity of the catalyst and the speed at which the polymerization is intended to proceed. In general, the curing catalyst is used in an amount of from 0.01 parts per 100 parts of resin (p.h.r.) to about 1.0 p.h.r., more specifically, from about 0.01 p.h.r. to about 0.5 p.h.r. and, most specifically, from about 0.1 p.h.r. to about 0.5 p.h.r. In one embodiment herein it will be understood herein that parts of resin relates to the parts of curable epoxy resin described herein, i.e., the total amount of the curable composition excluding catalyst, (total grams of epoxy+ Compound (I) and any other components present other than the curing catalyst=100% and then taking 100 grams of this is equal to 100 parts of resin); catalyst is added in above ranges to 100 parts of this total weight amount Preferably, a Lewis acid is also employed in any of the curable epoxy resin compositions of the present invention described herein, especially when the catalyst is particularly a heterocyclic nitrogen-containing compound.

The Lewis acids useful in the present invention include for example one or a mixture of two or more halides, oxides, hydroxides and alkoxides of zinc, tin, titanium, cobalt, manganese, iron, silicon, aluminum, and boron, for example Lewis acids of boron, and anhydrides of Lewis acids of boron, for example boric acid, metaboric acid, optionally substituted boroxines (such as trimethoxyboroxine), optionally substituted oxides of boron, alkyl borates, boron halides, zinc halides (such as zinc chloride) and other Lewis acids that tend to have a relatively weak conjugate base. Preferably the Lewis acid is a Lewis acid of boron, or an anhydride of a Lewis acid of boron, for example boric acid, metaboric acid, an optionally substituted boroxine (such as trimethoxy boroxine, trimethyl boroxine or triethyl boroxine), an optionally substituted oxide of boron, or an alkyl borate. The most preferred Lewis acid is boric acid. These Lewis acids are very effective in curing epoxy resins when combined with the heterocyclic nitrogen-containing compounds, referred to above.

The Lewis acids and amines can be combined before mixing into the formulation or by mixing with the catalyst in situ, to make a curing catalyst combination.

The amount of the Lewis acid employed is preferably at least 0.1 mole of Lewis acid per mole of heterocyclic nitrogen compound, more preferably at least 0.3 mole of Lewis acid per mole of heterocyclic nitrogen-containing compound.

The curable compositions of the present invention may optionally have boric acid and/or maleic acid present as a cure inhibitor. In that case, the curing agent is preferably a polyamine or polyamide. The amount of cure inhibitor will be known by those skilled in the art.

The curable compositions of the present invention may also optionally contain one or more additional flame retardant additives including, for example, red phosphorus, encapsulated red phosphorus or liquid or solid phosphorus-containing compounds, for example, "EXOLIT OP 930", EXOLIT OP 910 from Clariant GmbH and ammonium polyphosphate such as "EXOLIT 700" from Clariant GmbH, a phosphite, or phosphazenes; nitrogen-containing fire retardants and/or synergists, for example melamines, melem, cyanuric acid, isocyanuric acid and derivatives of those nitrogen-containing compounds; halogenated flame retardants and halogenated epoxy resins (especially brominated epoxy resins); synergistic phosphorus-halogen containing chemicals or compounds containing salts of organic acids; inorganic metal hydrates such as $Sb_2O_3$, $Sb_3O_5$, aluminum trihydroxide and magnesium hydroxide such as "ZEROGEN 30" from Martinswerke GmbH of Germany, and more preferably, an aluminum trihydroxide such as "MARTINAL TS-610" from Martinswerke GmbH of Germany; boron-containing compounds; antimony-containing compounds; silica and combinations thereof.

When additional flame retardants which contain phosphorus are present in the composition of the present invention, the phosphorus-containing flame retardants are preferably present in amounts such that the total phosphorus content of the epoxy resin composition is from 0.2 wt. percent to 5 wt. percent.

The curable compositions of the present invention may also optionally contain other additives of a generally conventional type including for example, stabilizers, other organic or inorganic additives, pigments, wetting agents, flow modifiers, UV light blockers, and fluorescent additives. These additives can be present in amounts of from 0 to 5 weight-percent and is preferably present in amounts less than 3 weight percent.

The flame resistant epoxy resin is preferably free of bromine atoms, and more preferably free of halogen atoms.

The compositions described above are useful for making coating formulations, encapsulation, composites, and adhesives, molding, bonding sheets, and laminated plates. The compositions of the present invention can be used to make composite materials by techniques well-known in the industry, such as by pultrusion, molding, encapsulation, or coating. As an illustration, a coating formulation may comprise (i) Compound (I), and/or Compounds (V)-(XI) (ii) a solid epoxy resin, and (iii) a hardener such as an amine or phenolic hardener. The amounts of hardener will be known by those skilled in the art.

The present invention is particularly useful for making B-staged prepregs, laminates, bonding sheets, and resin coated copper foils by well known techniques in the industry.

Ignition-Resistant Thermoplastic Resins (Thermoplastic Resin Composition)

In another embodiment of the present invention, the phosphorus-containing product, Compound (I), and/or Compounds (V)-(XI) are used to make phosphorus-containing ignition resistant thermoplastic resins.

A halogen-free ignition-resistant thermoplastic resin composition are obtainable by blending (i) the phosphorus-containing compound, Compound (I), and/or Compounds (V)-(XI) according to the present invention with (ii) at least one thermoplastic resin, and optionally any one or more of the optional components described for the thermosetting (e.g., epoxy) resin composition described herein.

Typical thermoplastic polymers include, but are not limited to, polymers produced from vinyl aromatic monomers and hydrogenated versions thereof, including both diene and aromatic hydrogenated versions, including aromatic hydrogenation, such as styrene-butadiene block copolymers, polystyrene (including high impact polystyrene), acrylonitrile-butadiene-styrene (ABS) copolymers, and styrene-acrylonitrile copolymers (SAN); polycarbonate (PC), ABS/PC compositions, polyethylene terephthalate, epoxy resins, hydroxy phenoxy ether polymers (PHE), ethylene vinyl alcohol copolymers, ethylene acrylic acid copolymers, polyolefin carbon monoxide interpolymers, chlorinated polyethylene, polyolefins (for example, ethylene polymers and propylene polymers, such as polyethylene, polypropylene, and copolymers of ethylene and/or propylene with each other or with an alpha-olefin having at least 4, more preferably at least 6, and preferably up to 12, and more preferably up to 8, carbon atoms), cyclic olefin copolymers (COC's), other olefin copolymers (especially copolymers of ethylene with another olefin monomer, such as from 1 to 12 carbon atom alken-1-yl groups) and homopolymers (for example, those made using conventional heterogeneous catalysts), polyphenylene ether polymers (PPO) and any combination or blend thereof.

Thermoplastic polymers are well-known by those skilled in the art, as well as methods for making them. In one embodiment, the thermoplastic polymer is a rubber-modified monovinylidene aromatic polymer produced by polymerizing a vinyl aromatic monomer in the presence of a dissolved elastomer or rubber.

The thermoplastic polymer or polymer blend is employed in the halogen-free ignition resistant polymer compositions of the present invention in amounts of at least 35 parts by weight, preferably at least 40 parts by weight, more preferably at least 45 parts by weight, and most preferably at least 50 parts by weight based on 100 parts by weight of the halogen-free ignition resistant polymer composition of the present invention. In general, the thermoplastic polymer component is employed in amounts less than or equal to 99 parts by weight, preferably less than or equal to 95 parts by weight, more preferably less than or equal to about 90 parts by weight, and most preferably less than or equal to about 85 parts by weight based on 100 parts by weight of the halogen-free ignition resistant polymer composition of the present invention.

In one embodiment, the halogen-free ignition resistant polymer composition of the present invention comprises Compound (I) and/or Compounds (V)-(XI) with a blend of two thermoplastic polymers wherein at least one of the thermoplastic polymers is for example a polyphenylene ether. Polyphenylene ethers are made by a variety of well known catalytic and non-catalytic processes from corresponding phenols or reactive derivatives thereof.

When used in combination with another thermoplastic polymer, the polyphenylene ether resin is preferably employed in the halogen-free ignition resistant polymer compositions of the present invention in amounts of at least 5 parts by weight, preferably 10 part by weight, more preferably at least 12 parts by weight, more preferably at least 15 parts by weight, and most preferably at least 18 parts by weight to 30 parts by weight, preferably to 28 parts by weight, more preferably to 25 parts by weight, based on 100 parts by weight of the halogen-free ignition resistant polymer composition of the present invention. The thermoplastic and polyphenylene ether polymer can be prepared as a blend prior to incorporation into the composition of the present invention, or each polymer can be incorporated individually.

The compositions of the present invention may include other additives such as modifiers that include compounds containing functionalities which will enhance the mechanical properties of the composition and are compatible with the thermoplastic resin. For thermoplastic resins such as monovinylidene aromatics and conjugated dienes, such functionalities might include, but are not limited to, butadienes, styrene-maleic anhydrides, polybutadiene-maleic anhydride copolymers, carboxylic acid terminated butadienes, and carboxylic acid functionalized polystyrenes. Any combination of modifiers can be used in modifying the phosphorus element-containing epoxy compounds.

The amount of Compound (I), and/or Compounds (V)-(XI) used in the ignition resistant thermoplastic polymer composition of the present invention is typically at least 1 weight-percent, generally at least 5 weight-percent, preferably at least 10, more preferably at least 15, and most preferably at least 20, weight-percent and less than 50, preferably less than 45, more preferably less than 40 and most preferably less than 35, weight-percent, based on the total weight of the ignition resistant polymer composition.

The thermoplastic resin compositions herein can contain any of the components and or ranges of amounts of components described herein for the thermosetting composition, the epoxy resin composition, or the hybrid compositions and vice-versa and of the thermoplastic composition, i.e., any of the components and or amounts of the components of the thermoplastic composition described herein can be used in any of the thermosetting composition, the epoxy resin composition, or the hybrid compositions described herein.

Preparation of the ignition resistant thermoplastic polymer composition of the present invention can be accomplished by any suitable mixing means known in the art, including dry blending the individual components and subsequently melt mixing, either directly in the extruder used to make the finished article or pre-mixing in a separate extruder. Dry blends of the compositions can also be directly injection molded without pre-melt mixing.

When softened or melted by the application of heat, the ignition resistant thermoplastic polymer composition of this invention can be formed or molded using conventional techniques such as compression molding, injection molding, gas assisted injection molding, calendaring, vacuum forming, thermoforming, extrusion and/or blow molding, alone or in combination. The ignition resistant thermoplastic polymer composition can also be formed, spun, or drawn into films, fibers, multi-layer laminates or extruded sheets, or can be compounded with one or more organic or inorganic substances, on any machine suitable for such purpose.

In one embodiment, the thermoplastic compositions of the present invention can be utilized in the preparation of foam. The ignition resistant thermoplastic polymer composition is extruded into foam by melt processing it with a blowing agent to form a foamable mixture, extruding said foamable mixture through an extrusion die to a region of reduced pressure and allowing the foamable mixture to expand and cool. Conventional foam extrusion equipment, such as screw extruders, twin screw extruders and accumulating extrusion apparatus can be used.

In another embodiment of the present invention, the halogen-free ignition resistant thermoplastic polymer composition of the present invention may optionally include, in addition to Compound (I), and/or Compounds (V)-(XI) other phosphorus-containing compounds. Optionally, the thermoplastic composition of the present invention may also include other flame retardant additives which can be phosphorus or non-phosphorus materials as described above.

The amount of optional phosphorus-containing compounds, other than Compound (I), and/or Compounds (V)-(XI) and/or the optional flame retardant additives used in the composition of the present invention may be from 0 up to 30 weight percent. The amount of optional phosphorus-containing component, other than Compound (I), and/or Compounds (V)-(XI) when present, is preferably at least 1 weight-percent and preferably up to 30 weight-percent based on the total weight of the thermoplastic resin.

The amount of component, Compound (I), and/or Compounds (V)-(XI) is preferably at least 5 weight-percent and preferably up to 20 weight-percent, based on the total weight of the thermoplastic resin.

The ignition resistant thermoplastic resin is preferably substantially free of bromine atoms, and more preferably completely free of halogen atoms.

The halogen-free ignition resistant thermoplastic polymer compositions of the present invention are useful to fabricate numerous useful articles and parts. Some of the articles which are particularly well suited include television cabinets, computer monitors, related printer housings which typically requires to have excellent flammability ratings. Other applications include automotive and small appliances.

Ignition-Resistant Thermosetting Composition (Thermosetting Composition)

In another embodiment of the present invention, the phosphorus-containing product, Compound (I), and/or Compounds (V)-(XI) is used to make a phosphorus-containing ignition resistant thermosetting composition, e.g., in one non-limiting embodiment wherein the thermoset polymer is in addition to or other than epoxy.

A halogen-free ignition-resistant thermosetting composition is obtainable by blending (i) the phosphorus-containing compound, Compound (I), and/or Compounds (V)-(XI) according to the present invention with (ii) at least one thermosetting system. Examples of thermosetting systems are epoxy, polyurethane, polyisocyanates, benzoxazine ring-containing compounds, unsaturated resin systems containing double or triple bonds, polycyanate ester, bismaleimide, triazine, bismaleimide and mixtures thereof.

The thermoset resin compositions herein can contain any of the components and or ranges of amounts of such components described herein for the curable epoxy resin composition, the thermoplastic composition or the hybrid compositions and vice-versa and of the thermoset resin composition, i.e., any of the components and or amounts of the components of the thermoset composition described herein can be used in any of the epoxy composition, the thermoplastic resin composition, or the hybrid compositions described herein.

Ignition-Resistant Thermoplastic/Thermosetting Hybrid Systems (Hybrid Composition)

In another embodiment of the present invention, the phosphorus-containing product, Compound (I), and/or Compounds (V)-(XI) is used to make phosphorus-containing ignition resistant hybrid resin system that contains both a thermoplastic and a thermosetting system.

The hybrid ignition-resistant thermoplastic and thermosetting compositions are obtainable by blending (i) the phosphorus-containing compound, Compound (I), and/or Compounds (V)-(XI) according to the present invention with (ii) a thermoplastic resin and (iii) a thermosetting system. Examples of thermoplastic resins are polyphenylene oxide (PPO), mixtures thereof, and others as described above. Examples of thermosetting systems are epoxy, polyurethane, polyisocyanates, benzoxazine ring-containing compounds, unsaturated resin systems containing double or triple bonds, polycyanate ester, bismaleimide, triazine, bismaleimide and mixtures thereof. The hybrid ignition-resistant thermoplastic and thermosetting composition can contain any of the optional components and amounts thereof described in the subject disclosure.

The amount of thermoplastic resin in the hybrid composition can be from about 20 to about 95 and preferably from about 30 to about 80, while the amount of thermoset resin can be from about 10 to about 20 and more preferably from about 30 to about 40 wherein said amounts are based on the total amount of thermoplastic and thermoset resin employed.

The hybrid resin compositions herein can contain any of the components and or ranges of amounts of components described herein for the epoxy resin composition, the thermosetting resin composition or the thermoplastic resin composition and vice-versa any of the epoxy resin composition, the thermosetting resin composition and the thermoplastic resin composition can contain any of the components and or amounts of the components of the hybrid resin composition described herein.

In one embodiment herein there is provided an article that contains any of the composition(s) described herein. In one embodiment the article herein can be used in lead free soldering applications and electronic devices, e.g., printed wiring board applications, specifically the article can be a prepreg and/or a laminate. In one specific embodiment there is provided a laminate and/or a prepreg that contains any one or more of the compositions described herein. In one other embodiment there is provided herein a printed wiring board, optionally a multilayer printed wiring board, comprising one or more prepreg(s) and/or a laminate (e.g., either uncured, partially cured or completely cured) wherein said prepreg(s) and/or laminate comprise any one or more of the compositions described herein. In one embodiment there is provided a printed wiring board comprising a prepreg and/or a laminate wherein said prepreg and/or laminate comprises any one of the compositions described herein.

Partial curing as used herein can comprise any level of curing, short of complete cure, and will vary widely depending on the specific materials and conditions of manufacture as well as the desired end-use applications. In one specific embodiment, the article herein can further comprise a copper foil. In one embodiment the article can comprise a printed wiring board. In one embodiment there is provided an FR-4 laminate which comprises a prepreg and/or laminate of the invention. In a more specific embodiment there is provided a printed circuit board comprising an FR-4 laminate, wherein the FR-4 laminate comprises a prepreg or laminate of the invention.

In one embodiment herein there is provided a process of making a laminate that contains any of the compositions described herein which process comprises impregnating the respective composition(s) into a filler material, e.g., a glass fiber mat to form a prepreg, followed by processing the prepreg at elevated temperature and/or pressure to promote partial cure to a B-stage and then laminating two or more of said prepregs to form said laminate. In one embodiment said laminate and/or prepreg can be used in the applications described herein, e.g., printed wiring boards.

There is provided herein that any of the compositions described herein are useful for making a prepreg and/or laminate with a good balance of laminate properties and thermal stability, such as one or more of high $T_g$ (i.e. above 130° C.), $T_d$ of 330° C. and above, $t_{288}$ of 5 minutes and above, a flame resistance rating of V-0, good toughness, and good adhesion to copper foil. In recent years $T_d$ has become one of the most important parameters, because the industry is changing to lead-free solders which melt at higher temperature than traditional tin-lead solders.

In one embodiment herein the compositions described herein can be used in other applications, e.g., encapsulants for electronic elements, protective coatings, structural adhesives, structural and/or decorative composite materials in amounts as deemed necessary depending on the particular application.

In yet a further embodiment herein there is provided a method of making a halogen-free curing agent for thermo- setting resins, e.g., for epoxy resins, made in one non-limiting embodiment by the method described in reaction mechanism (A) below:

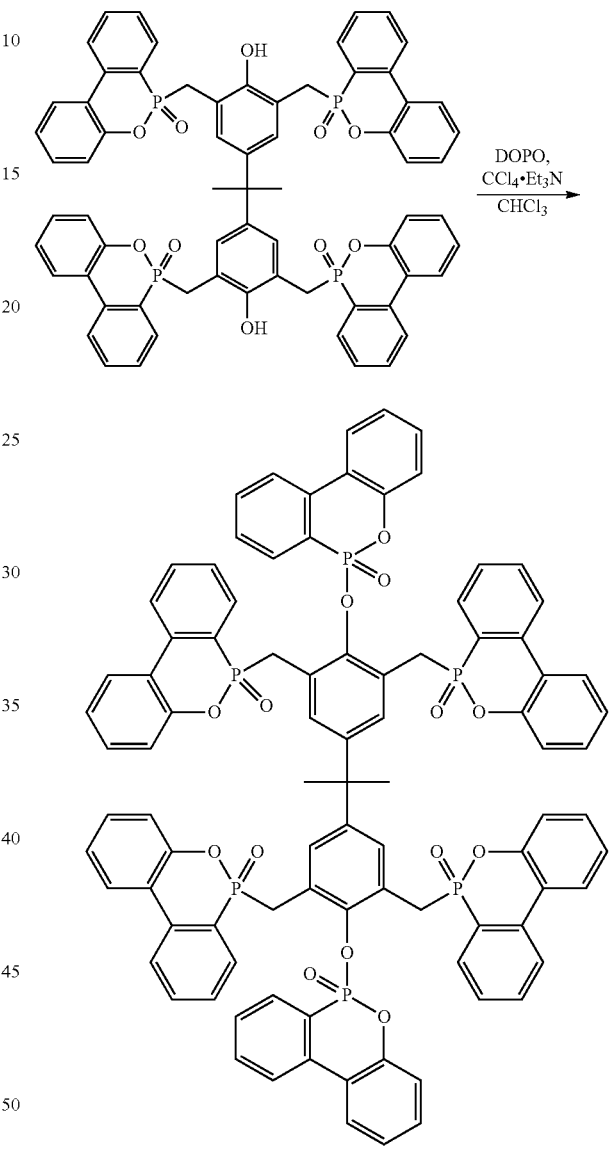

In one non-limiting embodiment, the method of making the halogen-free curing agent of formula (I) and/or (V)-(XI) herein can comprise reacting any phospha-phenanthrene-alkyl-substituted, hydroxy-substituted, and optionally alkylene substituted aromatic with an alkoxylated phospha-phenanthrene compound in the presence of at least one hydrocarbon solvent and a nitrogen based catalyst to produce compounds of the general formula (I) and/or (V)-(XI).

In one non-limiting embodiment herein the method of making the halogen-free curing agent of formula (I) and/or (V)-(XI) herein can comprise the following general reaction mechanism:

phospha-phenanthrene-alkyl-substituted, hydroxy-substituted, (and optionally alkylene substituted) aromatic + DOP-O-alkyl →

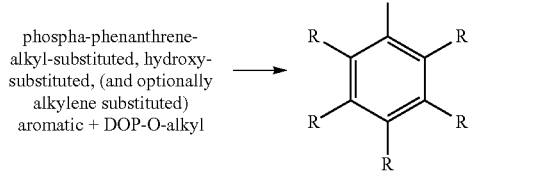
(I)

wherein the phospha-phenanthrene-alkyl-substituted, hydroxy-substituted, (and optionally alkylene substituted) aromatic and the DOP-O-alkyl are defined in various non-limiting embodiments below.

Phospha-Phenanthrene-Alkyl-Substituted, Hydroxy-Substituted, (and Optionally Alkylene Substituted) Aromatic One non-limiting example of a general formula is (A):

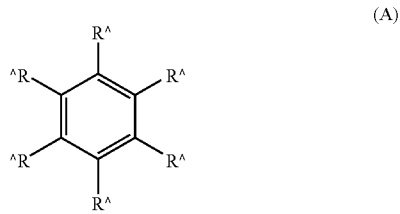
(A)

wherein each $R^{\char`\^}$ is independently selected from H; —OH; a phosphinate moiety of the formula (II) as defined herein; a phosphonate moiety of the general formula (III) as defined herein; and, a substituted aryl moiety of the general formula (IV) as defined herein, wherein at least one $R^{\char`\^}$ is —OH and at least one $R^{\char`\^}$ is a group of the general formula (II).

DOP-O-Alkyl:

In one non-limiting embodiment the DOP-O-Alkyl is selected from the general formulae (B):

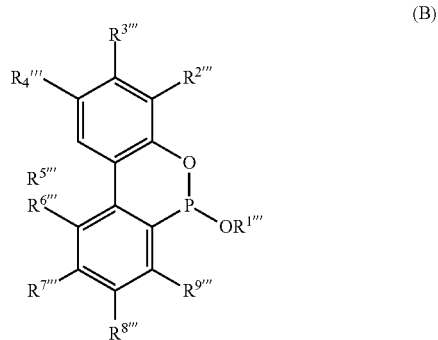
(B)

where $R^{1'''}$ is a linear or branched alkyl group containing from 1 to 8 carbon atoms, more specifically from 1 to about 4 carbon atoms; each of $R^{2'''}$-$R^{9'''}$ is independently a hydrogen atom or a hydrocarbyl group that may contain on or more heteroatom such as O, S, N, P or Si provided that not more than 3 of $R^{2'''}$-$R^{5'''}$ are hydrogen atoms, and each of $R^1$-$R^9$ independently contains less than 7 carbon atoms.

Reagents and Solvent

The reagents $CCl_4$ and $CH_3Cl$ are indicated in the reaction mechanism above are one embodiment of the invention although the solvent can be any organic, preferably aprotic, solvent. The solvent may be polar or non-polar. Exemplary of polar aprotic solvents are dimethyl formamide, dimethyl acetamide and N-methylpyrrolidone. Preferred solvents are aprotic and non-polar, conveniently aliphatic hydrocarbons, typically heptane, octane, cyclohexane, decalin, mineral oil distillates, such as petroleum ether, ligroin, kerosene, aromatic hydrocarbons such as benzene, toluene, or xylenes, or mixtures of said solvents. The amount of solvent can be set at from about 5 wt % to about 90 wt %, more specifically from about 20% to about 70%.

Catalyst

The catalyst indicated above is triethylamine, although any nitrogen based catalyst is suitable. Such as the non-limiting examples of amides, imides, amines, quaternary ammonium salts and ureas. The preferred catalysts are the N,N-disubstituted amides such as N,N-dimethyl formamide, N-methylpyrrolidone, etc., the N-monosubstituted amides such as N-methyl formamide, N-methyl acetamide, etc., the tertiary amines such as pyridine, triethylamine, etc., secondary amines such as pyrrolidine, diethylamine, etc., and substituted ureas such as tetramethyl urea. The amount of catalyst employed can be from about 500 ppm to about 10,000 ppm, more specifically from about 1,000 ppm to about 5,000 ppm.

The amounts of (A) and (B) are used in equimolar amounts but an excess of up to 20%, preferably up to 10% of one or more of (A) or (B), can be useful. The reaction temperature of the above reaction mechanism range from room temperature (e.g., 25° C.) up to about 200° C., preferably from 50° C. to about 140° C. and most preferably from 60° C. to about 120° C.

The following examples are used to illustrate the present invention.

EXAMPLES

Synthesis Example 1

1. DOPO-BPA material was reacted with DOPO-Cl (9,10-Dihydro-9-oxa-10-phosphaphenanthrene-10-chloride) via an Atherton-Todd reaction:

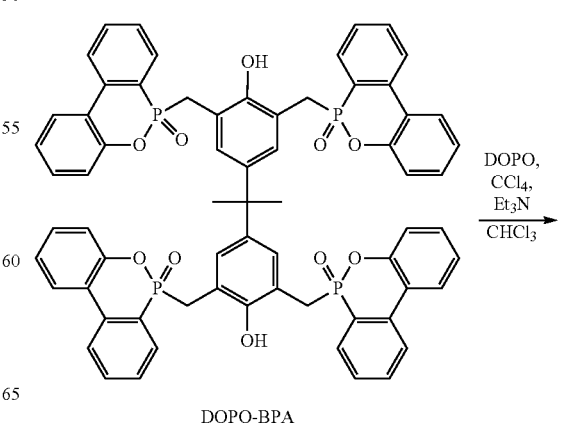

DOPO, $CCl_4$, $Et_3N$ $CHCl_3$

DOPO-BPA

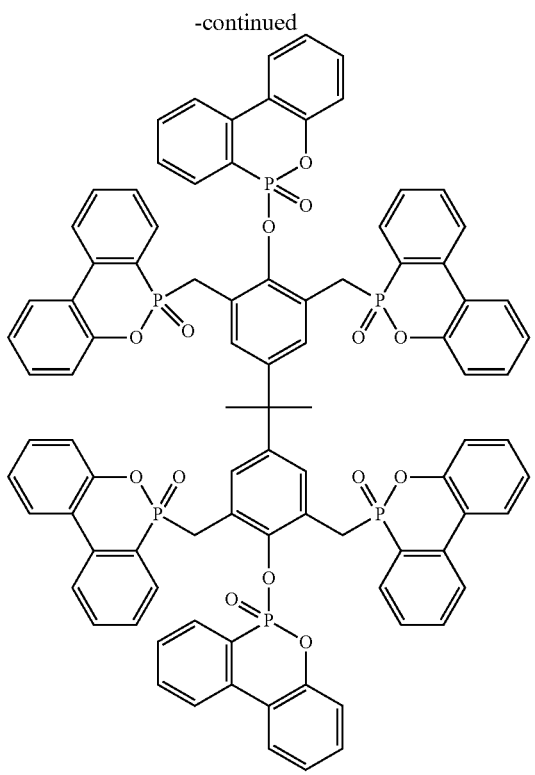

Compound 1

Synthesis Example 1

DOPO-BPA material (4.37 g, 4.23 mmol, 1 equivalent) was dissolved in 5 mL of anhydrous chloroform and DOPO (9,10-Dihydro-9-oxa-10-phosphaphenanthrene 10-oxide) (2.01 g, 9.3 mmol, 2.2 equivalent) dissolved in 5 mL of chloroform was transferred to the reaction mixture. Triethylamine (3 mL, 21.13 mmol, 5 equivalents) was added at room temperature to the reaction mixture. The mix was cooled to 0° C., tetra chloromethane (0.98 mL, 10.14 mmol, 2.4 equivalents) in 3 mL of chloroform was added drop-wise and stirred for 2 hours, then warmed up to room temperature and stirred overnight. The crude mixture was diluted with chloroform, the organic phase was washed with di-water, ammonium chloride, 0.2 M of hydrochloric acid (×2), di-water (×2), then with half and half sodium bicarbonate and brine solution. The organic phase was dried over $MgSO_4$, filtered and concentrated to yield 5.22 g of product with 84% yield.

Example 2 Laminate Preparation

Laminate Example 2

1. Materials

Compound 1 from synthesis example 1 was used as a curing agent. The epoxy used in this investigation included a phenol novolac epoxy, DEN 438, from Dow Chemical and cresol novolac epoxy, EPON 164, from Hexion chemicals. A phenolic novolac, SD-1708, was used as a co-curing agent in the formulation. 2-methyl imidazole from Air Products was used as the curing accelerator. Dowanol was used as a solvent during the preparation of the varnish. All the materials information is listed in Table 1.

2. Preparation of Varnish

The varnish formulation is given in Table 2. Weighed amounts of epoxy resin and curing agent were added to a glass jar equipped with a mechanical stirrer. Dowanol was added such that the total solids content of the varnish formulation was close to 66.67%. Addition of dowanol helps in lowering the viscosity of the varnish, aids in the manual brushing of the glass cloth, and maintaining the solids content of the varnish. The 2-mI accelerator was finally added to the varnish. The varnish was continuously stirred for several hours until a uniform solution was obtained. A DSC heating run with 10° C./min up to 250° C. was used to determine the curing kinetics of the formulation and the maximum curing temperature occurred close to 197° C., which is shown in FIG. 1. The varnish gel time was tested on a hot plate at 171° C. The varnish gel time was 255 seconds with this formulation.

3. Manufacturing of Prepreg

The glass fabric (10.5×11.0 inch) was manually brushed with varnish on both sides at room temperature. The glass fabrics were hanged overnight in the laboratory for the slow evaporation of the dowanol. Later, the glass fabrics were placed in a preheated air circulated oven at 165° C. for 3'40", where the rest of the solvent would evaporate and the resin would be cured to a B-stage. Different drying times were applied and the obtained prepregs were tested for resin flow. The resin flow was measured according to IPC-TM-650 test 2.3.16.2. Prepregs were made with this varnish and dried at 165° C. for 3'40", which gives a resin flow close to 25-30.0%. Also, the resin content was controlled to be over 45-50%, which is determined through the difference in weight between the glass fabric and the prepreg. Small sections of the prepregs (2.5×2.5 inch) were dried in the oven at 165° C. for 3'40" minutes and at 15 minutes to determine the residual solvent content. Most of the solvent was not present in the prepregs as determined by calculating the difference in weights of the prepregs before and after placing them in the oven at 165° C. The prepreg gel time was determined by collecting the fusible, thermoplastic resin by crushing the prepreg in a zip-lock bag. The collected resin was placed on the hot-plate at 171° C. and the gel time determined. The prepreg properties are shown in the table below:

| Varnish and prepreg properties using the formulation of Compound 1 shown in Table 2 | IPC-TM-650 No. | Value |
| --- | --- | --- |
| Resin content (wt %) | 2.3.16.2 | 45-50 |
| Varnish gel time (sec) | 2.3.18 | 255 |
| Prepreg gel time (sec) | 2.3.18 | 180 |
| Flow (%) | 2.3.17 | 25-30 |

The treating conditions chosen resulted in the evaporation of all the solvent and the prepregs have <2.5 wt % of residual solvent.

4. Pressing the Laminate

Figure 2:
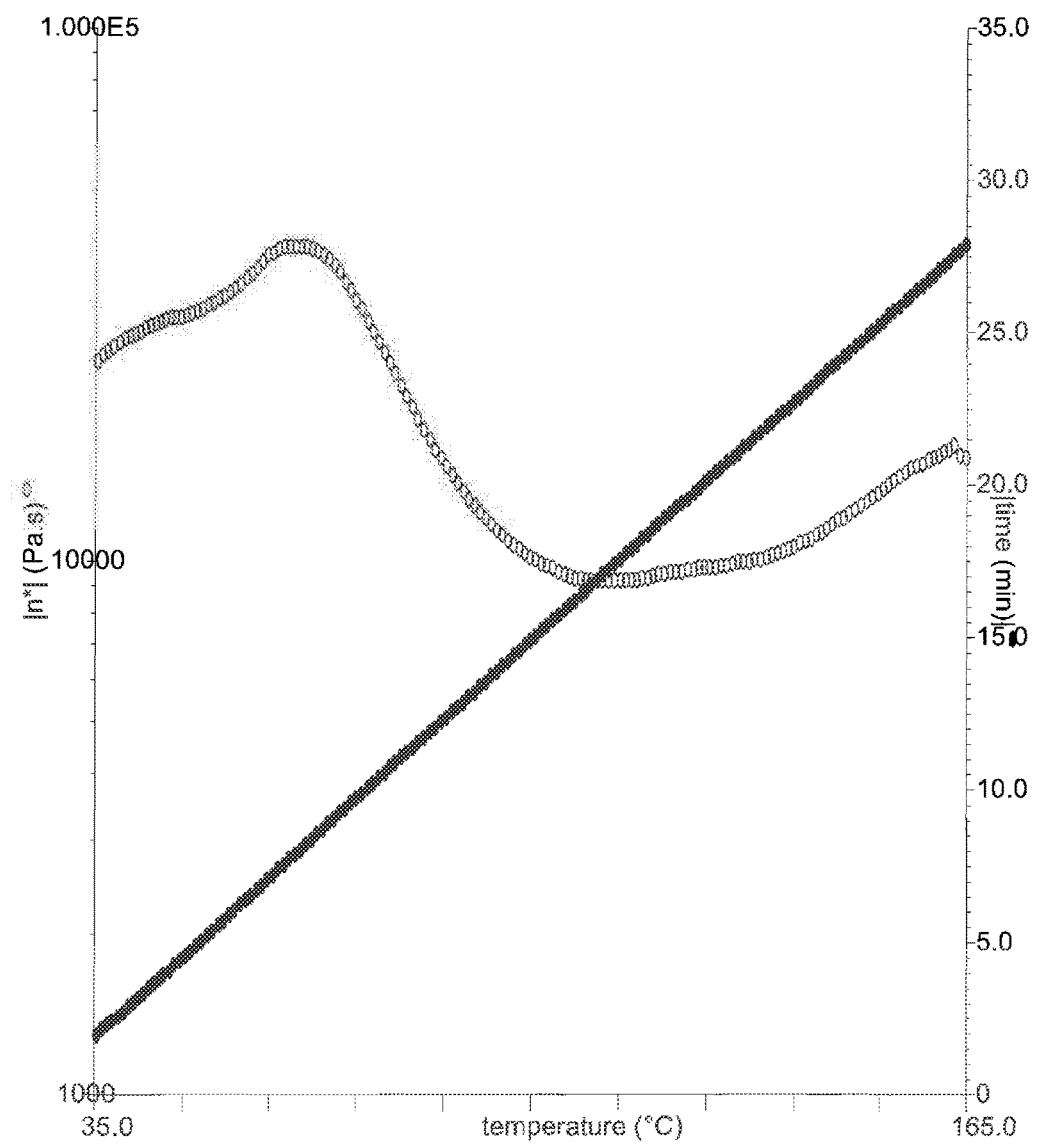
FIG. 2 is a graph of the dynamic viscosity (open circles) profile of a B-stage prepreg at a ramp rate (filled circles) of 5° C./min in a rheometer under continuous controlled strain and normal force conditions using the laminate of laminate Example 2.

A circular stack of 4 prepregs with a diameter of 25 mm was placed between the disposable Al plates to study the rheological behavior of the resin by electrically heating to 200° C. at 5° C./min in an AR2000ex Rheometer in-house. FIG. 2 shows the complex viscosity profile of the prepreg with rise in temperature of the B-staged resin system in an oscillatory testing mode. Based on the FIGS. 1 and 2, the curing cycle was designed to obtain a good wetting of the glass cloth. A low initial pressure of 10 psi was applied at 95° C. (the complex viscosity of the prepreg was around 12,000 pa-s) and sufficient to wet the glass fabric as studied during the preparation of various experimental epoxy laminates. Subsequently, the pressure dropped with raise in temperature and the pressure was raised back again to 10 psi at 110° C. A pressure of 20 psi was applied at 125° C., wherein the complex viscosity was close to 11,160 Pa-sec and the pressure was maintained at 20 psi even at 155° C. Finally, the pressure was raised for every 10 minutes at 195° C. until 260 psi was reached and the press was isothermally maintained at 195° C. for 90 minutes. Adopting the temperature and time of the B-stage system, 8 prepregs were prepared. The 8 prepregs were stacked together with a copper foil on the top and bottom of the stack. Then the assembly was placed between two stainless steel plates and put into a hydraulic press with 4 sheets of Kraft paper below and above the plates. The press was linearly heated to 195° C. and pressure was gradually increased from 10 psi to 260 psi during the heating process as described above. The laminate was cured at 195° C. for 90 min. After that, the press was cooled by turning on the cooling water to room temperature. The laminate showed a good resin flow and the thickness of the final laminate was close to 1.35 mm (without copper).

5. Flammability Test and Pressure Cooker Test

The flammability of the laminate (UL-94 ratings) was recorded by following ASTM D3601-06 procedure using an Atlas UL-94 burning chamber (V-0 being the highest possible rating). The copper foil was peeled off from the laminates according to IPC-TM-650, test 2.3.7.1. The pressure cooker test (PCT) was performed according to IPC-TM 650, test 2.6.16 with the following modifications: (a) specimens were exposed to the steam in autoclave for 30 minutes; (b) temperature of solder bath was held at 288° C., (c) specimens were dipped in the solder for 20 seconds.

6. Glass Transition and Thermal Decomposition Temperature of Laminate

Figure 3:
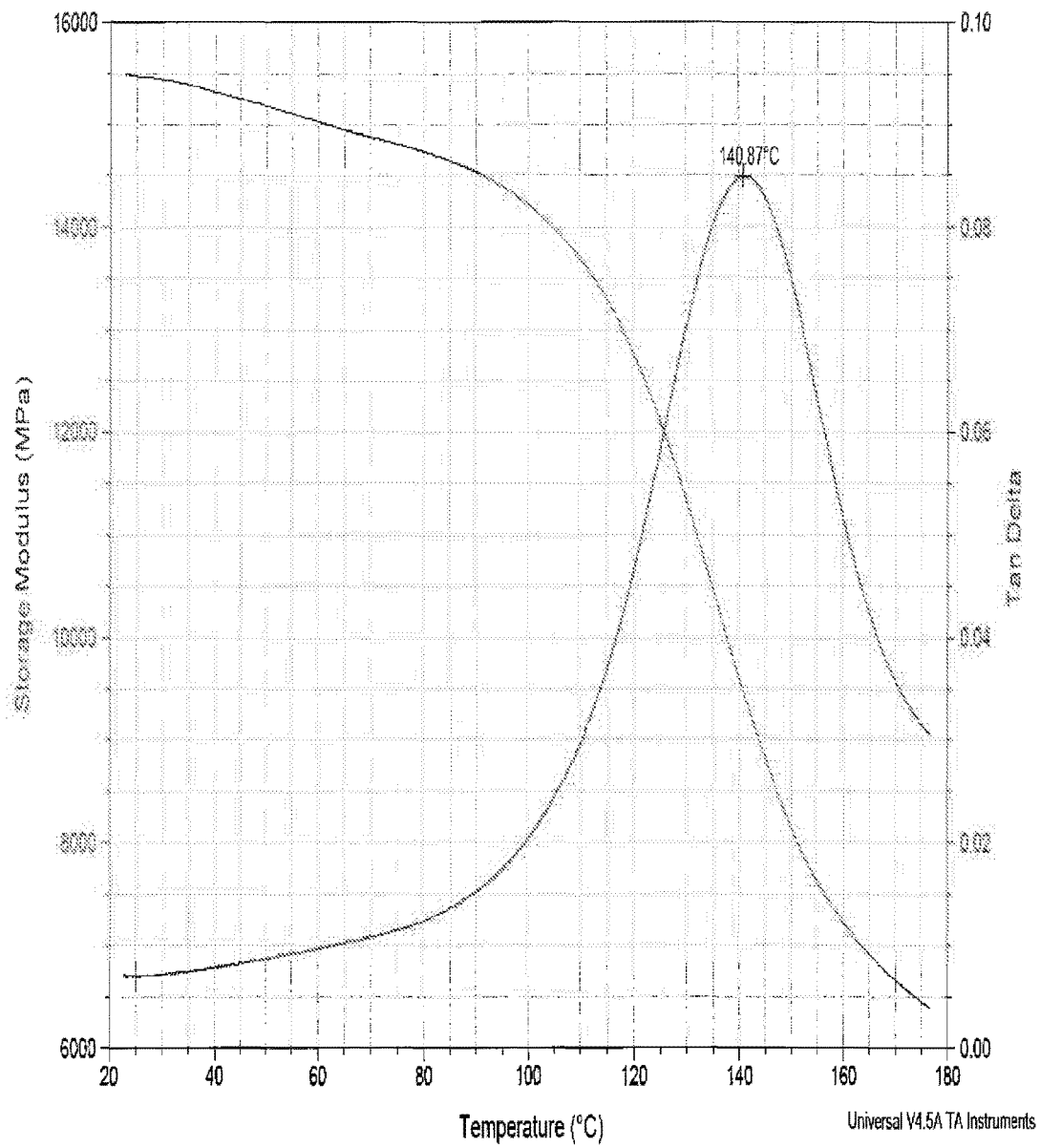
FIG. 3 is a graph demonastrating the dynamic mechanical analysis (DMA) measurement of the glass transition temperature (Tg) for the laminate prepared in laminate Example 2 (3° C./min).
Figure 4:
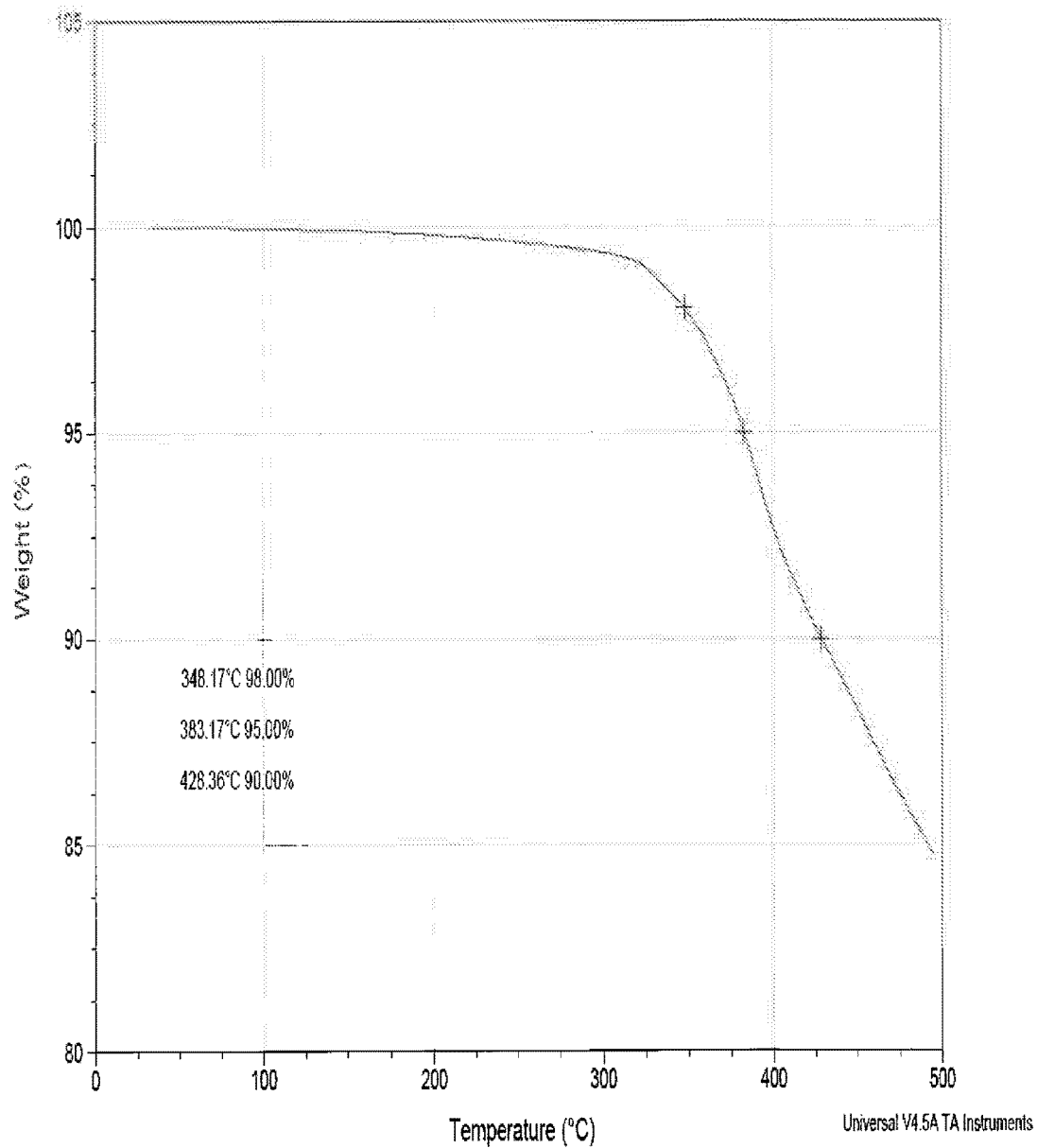
FIG. 4 shows the TGA plot of the cured epoxy (DEN438 and EPON164) and phenolic novolac SD1708 using the molecule (V) compound 1.

The glass transition temperature of the laminate was determined using DMA method. The test was conducted at 3° C./min with the heating run from room temperature up to 180° C. The $T_d$ of the laminate was measured with TGA. The test was carried out at 10° C./min with temperature up to 500° C. The DMA and TGA measurement results are shown in FIGS. 3 and 4 respectively.

7. Results

Compound 1 from Example 1 was explored as a curing agent for the epoxy laminate application. The Compound 1 was used as a curing agent together with phenolic novolac to cure multi-functional epoxy resins DEN 438 and EPON 164. The varnish formulation had a phosphorus content of 3.0% and solids content of around 66.67%. The varnish had a gel time of 255 seconds at 171° C. and the prepreg had a gel time close to 180 seconds at 171° C. Prepregs were made at 165° C. for 3'40" to achieve a resin flow of around 25.0-30.0% and a resin content of around 45-50% with negligible residual solvent. The dynamic complex viscosity profile of the prepreg was studied and the curing cycle was designed to prepare a laminate that had a final thickness of 1.35 mm (without copper). The laminate was rated as a V-0 with a maximum burn time of 8 seconds. The glass transition temperature of the laminate was around 141° C. and the thermal decomposition ($T_d$–5 wt % loss) of the laminate occurred at 383° C. as accessed from the TGA. In the PCT test the water uptake after 30 minutes was 0.41% and 0.48% respectively.

TABLE 1

Materials

| TRADE NAME (PRODUCER) | GENERAL INFO | FUNCTION |
| --- | --- | --- |
| Compound 1 | DOPO derivative | Curing agent |
| Epoxy resin (DEN 438, ex Dow) | Phenol novolac epoxy | Resin |
| Epoxy resin (EPON 164, ex Hexion) | Cresol novolac epoxy | Resin |
| Phenolic Novolac (SD-1708, ex momentive) | Phenolic novolac | Co-curing agent |
| 2-mI (ex Air Products) | 2-methyl imidazole | Catalyst |
| Dowanol (ex Fluka) | 1-methoxy 2-propanol | Solvent |

TABLE 2

Epoxy laminate formulation with Compound 1

| DEN 438 (g) | EPON 164 (g) | Compound 1 (g) | SD-1708 (g) | 2-mI (g) |
| --- | --- | --- | --- | --- |
| 22.02 | 26.91 | 29.79 | 21.28 | 0.05 |

TABLE 3

Test Methods

| PROPERTY | METHOD | APPARATUS |
| --- | --- | --- |
| Flammability vertical burning test at 1.6 mm | UL-94 | Atlas Chamber |
| Resin Flow Test | IPC-TM-650, test 2.3.16.2 | Paper Cutter |
| Pressure Cooker Test | IPC-TM 650, test 2.6.16 | Autoclave and Soldering Bath |
| Rheology (storage modulus and complex viscosity) | Rheological measurement | TA AR2000x |
| Curing Temperature | Differential Scanning Calorimetry | TA Q20 |
| Glass Transition Temperature (Tg) | Dynamic Mechanical Analysis | TA Q800 |
| Thermal Decomposition Temperature ($T_d$, 5%) | Thermogravimetric Analysis | TA Q500 |

TABLE 4

UL-94 flammability of epoxy laminate formulation with Compound 1

| | | Compound 1 | Unit | |
| --- | --- | --- | --- | --- |
| UL94 | Max flaming time | | sec | 8 |
| | Total flaming time | | sec | 9 |
| | Specimens dripped | | N° | 0 |
| | Specimens ignited cotton | | N° | 0 |
| | Specimens burned up to the clamp | | N° | 0 |
| | Rating | | | V0 |

While the present invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out the process of the invention but that the invention will include all embodiments falling within the scope of the appended claims.

The invention claimed is:
1. A compound having the general formula (I):

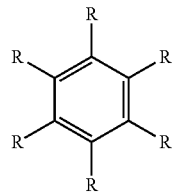

wherein each R is independently selected from H; —OH; an alkyl containing from 1 to about 8 carbon atoms;

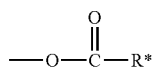

where R* is an alkyl group containing from 1 to 8 carbon atoms or a substituted or unsubstituted phenyl;
a phosphinate moiety of the formula (II):

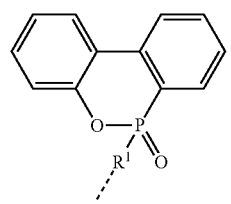

wherein $R^1$ is a divalent linear or branched alkylene moiety of from 1 to 3 carbon atoms, and the dashed line represents a bond to the structure of formula (I) above;
a phosphonate moiety of the general formula (III):

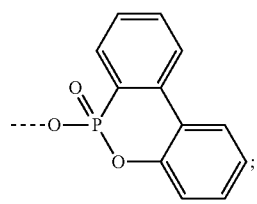

and,
a substituted aryl moiety of the general formula (IV):

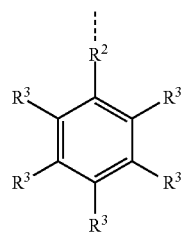

where $R^2$ is a divalent linear or branched alkylene moiety of from 1 to 4 carbon atoms, and the dashed line represents a bond to the structure of formula (I) above, and $R^3$ is defined the same as R except that $R^3$ cannot be the substituted aryl moiety of the general formula (IV) and at least one $R^3$ is a group of the formula (II);

and provided that the number of R groups of the formula (I) which are of the formula (II) are 1 or 2, the number of R groups of the formula (I) which are of the formula (III) are 1 or 2 and provided that none of the R groups or only one of the R groups of formula (I) are of the formula (IV) and further provided that when none of the R groups of the formula (I) are of the formula (IV), then the total number of R groups which are of the formula (II) and (III) can be up to 4, and if one of the R groups of the formula (I) is of the formula (IV) then the total number of R groups which are of the formula (II), (III) and (IV) are up to four.

2. The compound of claim 1 wherein the compound is selected from the fomulae (V)-(XI):

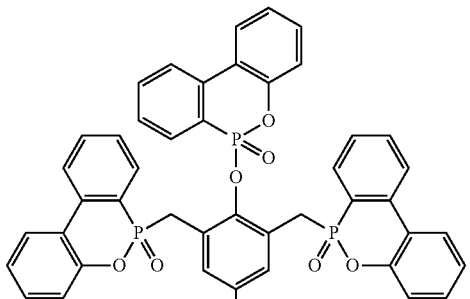

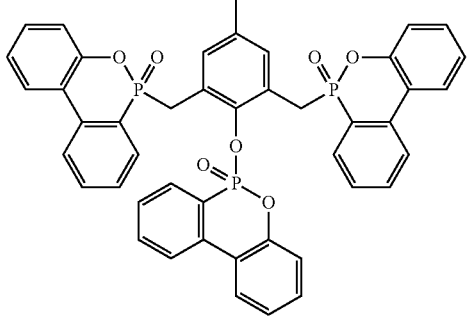

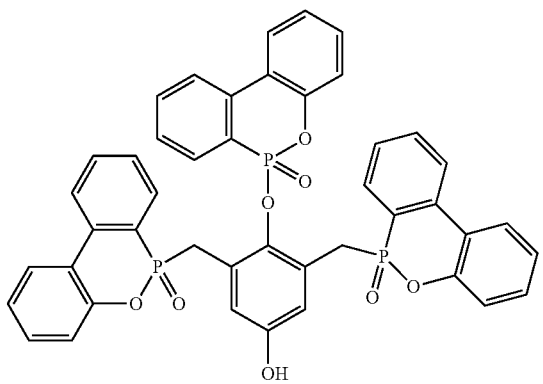

VII
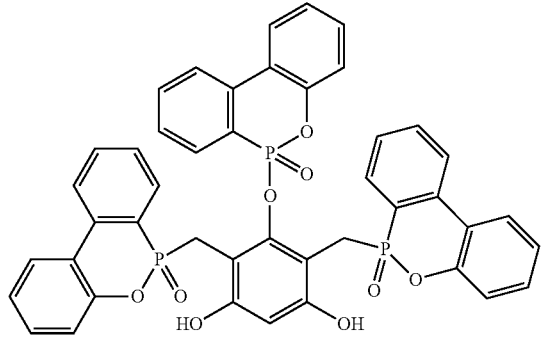

VIII
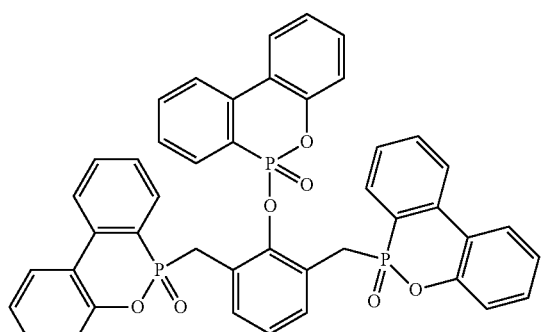

IX
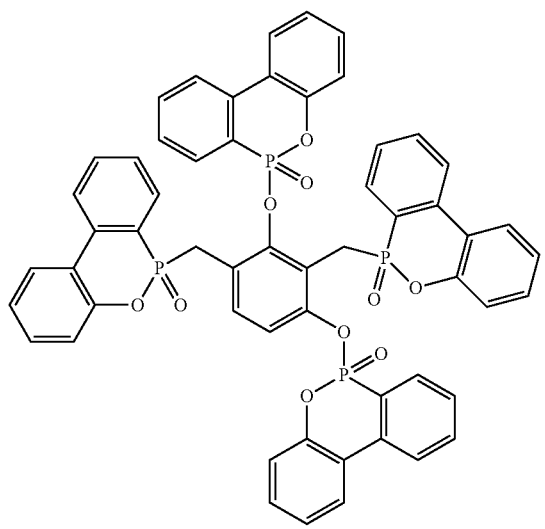

X
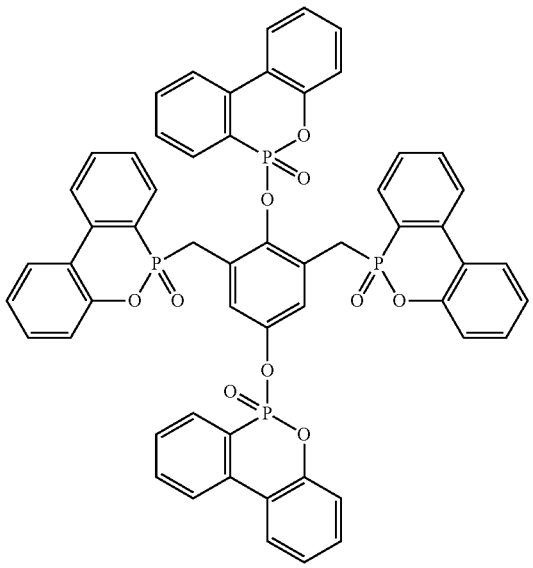

XI
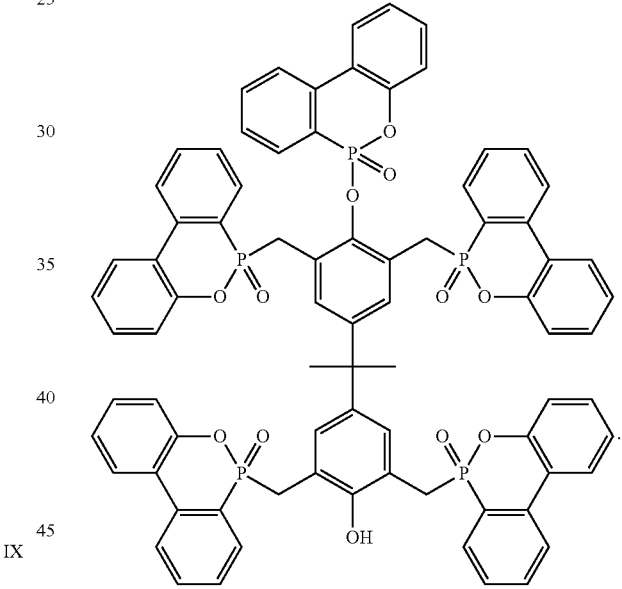

3. A composition comprising a thermosetting resin, from about 10 to about 150 parts by weight of the compound of claim 1 of formula (I) per 100 parts of the thermosetting resin, and optionally one or more of a co-crosslinker, a curing catalyst, a Lewis acid, a benzooxazine-containing compound, and optionally an inhibitor.

4. The composition of claim 3 wherein the thermosetting resin is an epoxy resin.

5. The composition of claim 3 wherein the thermosetting resin is selected from the group consisting of epoxy, polyurethane, polyisocyanates, benzoxazine ring-containing compounds, unsaturated resin systems containing double or triple bonds, polycyanate ester, bismaleimide, triazine, bismaleimide and mixtures thereof.

6. A composition comprising a thermoplastic resin, from about 10 to about 150 parts by weight of the compound of claim 1 of formula (I) per 100 parts by weight of thermoplastic resin, and optionally a co-crosslinker, optionally a Lewis acid, optionally a benzooxazine-containing compound, and optionally an inhibitor.

7. A composition comprising a thermoplastic resin, a thermosetting resin, from about 10 to about 150 parts by weight of the compound of claim 1 of formula (I) per 100 parts by weight of the combined weight of thermoplastic resin and thermosetting resin, and optionally a co-crosslinker, optionally a curing catalyst, optionally a Lewis acid, optionally a benzooxazine-containing compound, and optionally an inhibitor.

8. The composition of claim 3 wherein the compound of formula (I) is in the absence of halogen.

9. The composition of claim 3 formulated as any one of a coating formulation, an encapsulant, a composite, an adhesive, a molding a bonding sheet or a laminated plate.

10. An article comprising the composition of claim 3.

11. The article of claim 10 wherein said article can be used in lead free soldering applications and electronic devices.

12. The article of claim 10 wherein the article further comprises a copper foil.

13. The article of claim 12 wherein said article is a printed wiring board.

14. A prepreg comprising the composition of claim 3.

15. A laminate or a bonding sheet comprising the composition of claim 3.

16. A printed wiring board comprising prepreg of claim 14.

17. A printed wiring board comprising the laminate of claim 15.

18. A process of making a laminate that contains the composition of claim 3 comprising impregnating the composition into a filler material, to form a prepreg, followed by processing the prepreg at elevated temperature to promote partial cure to a B-stage and then laminating two or more of said prepregs at elevated pressure and temperature to form a laminate.

19. A printed wiring board made by the process of claim 18.

* * * * *